United States Patent [19]

Raleigh et al.

[11] Patent Number: 5,378,789
[45] Date of Patent: Jan. 3, 1995

[54] PHENOL-MODIFIED SILICONES

[75] Inventors: William J. Raleigh, Rensselaer; Donald S. Johnson, Scotia, both of N.Y.; Michael A. Lucarelli, Mattoon, Ill.; Gary C. Davis, Albany, N.Y.; James F. Hoover, Evansville, Ind.

[73] Assignee: General Electric Company, Waterford, N.Y.

[21] Appl. No.: 28,085

[22] Filed: Mar. 8, 1993

Related U.S. Application Data

[63] Continuation-in-part of Ser. No. 882,983, May 14, 1992, abandoned.

[51] Int. Cl.$^6$ .............................................. C08G 77/06
[52] U.S. Cl. .................................. 528/29; 528/43; 528/31; 528/37; 556/449; 556/461; 556/445; 525/474
[58] Field of Search ................... 556/449, 461, 445; 558/43, 29, 31, 37; 525/474

[56] References Cited

U.S. PATENT DOCUMENTS

| | | | |
|---|---|---|---|
| 3,419,634 | 12/1968 | Vaughn, Jr. | 260/824 |
| 3,419,635 | 12/1968 | Vaughn, Jr. | 260/824 |
| 4,032,511 | 6/1977 | Blount | 528/29 |
| 4,430,235 | 2/1984 | Chu et al. | 252/496 |
| 4,617,238 | 10/1986 | Crivello et al. | 428/452 |
| 4,745,169 | 5/1988 | Sugiyama et al. | 528/43 |
| 4,822,716 | 4/1989 | Onishi et al. | 430/192 |
| 4,871,816 | 10/1989 | Percec et al. | 525/393 |
| 4,946,921 | 8/1990 | Shirahata et al. | 528/39 |
| 4,952,657 | 8/1990 | Riding et al. | 528/27 |
| 5,138,012 | 8/1992 | Riding et al. | 525/478 |

OTHER PUBLICATIONS

"Silicones" Reprinted from *Encyclopedia of Polymer Science and Engineering*, 1989 pp. 235–236.

*Primary Examiner*—Melvyn I. Marquis
*Assistant Examiner*—Margaret W. Glass

[57] ABSTRACT

The present invention provides novel silicone compositions comprising phenol-modified branched and cyclic silicones which provide improved low temperature viscosity properties.

5 Claims, No Drawings

PHENOL-MODIFIED SILICONES

This is a continuation-in-part of application Ser. No. 07/882,983 filed on May 14, 1992, now abandoned. The present invention relates to silicone compositions. More particularly the present invention relates to silicone polymers which are modified with a phenolic group. Most particularly the present invention relates to silicone polymers which are modified with a eugenol group. The phenol-modified silicone polymers may be branched or cyclic systems.

BACKGROUND OF THE PRESENT INVENTION

Silicone compositions which are curable by hydrosilation reactions of silicon hydride precursors and terminally unsaturated olefins are well known to those of ordinary skill in the art and are discussed in the literature.

It has now been found that novel silicone compositions can be formed from the reaction of a hydride precursor with an olefinically substituted phenol, such as eugenol, synthesized by reacting a polydimethylsiloxane containing either methyltrisiloxy functionalities, cyclic tetramer functionalities or tetrasiloxy functionalities. These novel phenol-modified branched and cyclic silicone compositions provide improved low temperature viscosity properties over phenol-modified linear silicone compositions. Such improvements are shown in the working examples of the present specification.

SUMMARY OF THE PRESENT INVENTION

According to the present invention there is provided a silicone composition comprising a phenol-modified branched silicone of the general formula:

$$TD_x(Si(CH_3)_2M')_3$$

wherein T is a trifunctional alkyl siloxy unit of the general formula $RSiO_{3/2}$ where R is an alkyl group of from 1 to about 20 carbon atoms: D represents an alkyl siloxy unit of the general formula $R_2SiO_{2/2}$ where R is as defined above, x is 0 or an integer of greater than 0, preferably ranging from about 0 to about 300, most preferably from about 0 to about 100 and M' is a substituted phenol unit. More preferably, M' represents a phenol unit of the general formula

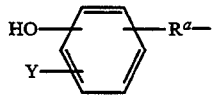

wherein $R^a$ is an alkylene group, and Y represents hydrogen, hydrocarbyl, hydrocarbylthio, hydrocarbyloxy or halogen. More preferred is where $R^a$ is an alkylene group containing from 2 to 12 carbon atoms and Y represents alkoxy or hydrogen. Most preferred is where $R^a$ is propylene and Y is methoxy. A particularly preferred phenol unit useful in the present invention is 4-propylene-2-methoxyphenol.

According to the present invention, there is also provided a silicone composition comprising phenol-modified cyclic silicones of the general formula:

$$(RM'SiO)_b$$

wherein R is an alkyl group of from 1 to about 20 carbon atoms, M' is as defined above, and b is an integer ranging from 3 to 8 inclusive.

According to the present invention there is provide a tetrafunctional silicone composition comprising phenol-modified branched silicones of the general formulae:

$$Q_pD_x(Si(CH_3)_2M')_y \text{ or } Q_p(Si(CH_3)_2M')_y(Si(CH_3)_2M'')_z \text{ or }$$

$$Q_pD_xD'_d(Si(CH_3)_2M')_y \text{ or } Q_pD_xD'_d(Si(CH_3)_2M')_y(Si(CH_3)_2M'')_z$$

wherein Q represents a tetrafunctional siloxy unit of the general formula $SiO_{4/2}$; D represents an alkyl siloxy unit of the general formula $R_2SiO_{2/2}$ where R is an alkyl group of from 1 to about 20 carbon atoms; D' represents a diorganosiloxy unit of the formula $R'_2SiO_{2/2}$ wherein each R' is independently an alkyl group of from 1 to about 20 carbon atoms, a vinyl group, a phenyl group, a cycloaliphatic group, or a phenol group, provided at least one R' group is not alkyl, M' is as defined above; p is an integer greater than 0; M" is an organic radical containing an alkene linkage containing at least two carbons bonded to the silicon atom: x is greater than or equal to 0; y and z are each 1 or greater provided that when the phenol-modified silicone contains no D or $D^1$ units y plus z equal no more than 4.

DETAILED DESCRIPTION OF THE PRESENT INVENTION

The present invention relates to novel phenol modified branched or cyclic silicones.

The phenol-modified silicones can be branched or cyclic and have the following general formulae:

$$TD_x(Si(CH_3)_2M')_3;$$

$$(RM'SiO)_b;$$

$$Q_pD_x(Si(CH_3)_2M')_y;$$

$$Q_p(Si(CH_3)_rM')_y(Si(CH_3)_2M'')_z;$$

$$Q_pD_xD'_d(Si(CH_3)_2M')_y$$

and $$Q_pD_xD'_d(Si(CH_3)_2M')_y(Si(CH_3)_2M'')_z$$

wherein T represents a trifunctional siloxy unit of the formula $RSiO_{3/2}$ where R is an alkyl group of from 1 to about 20 carbon atoms, D represents an alkyl siloxy unit of the general formula $R_2SiO_{2/2}$ wherein R is an alkyl group of from 1 to 20 carbon atoms, D' represents a diorgano-siloxy unit of the formula $R'_2SiO_{2/2}$ wherein each R' is independently an alkyl group of from 1 to about 20 carbon atoms, a vinyl group, a phenyl group, a cycloaliphatic group, or a phenol group, provided at least one R' group is not alkyl, M' is as defined above, Q represents a tetrafunctional siloxy unit of the general formula $SiO_{4/2}$, M" is as defined above, x is greater than or equal to 0, preferably ranging from 0 to about 300, more preferably ranging from about 0 to about 100 and p, b, y, z and are as defined above. Most preferably, R represents a methyl group.

In the case of the cyclic phenol modified silicones, it is contemplated that the composition may comprise a variety of cyclic silicones wherein b varies from 3 to 8, more preferably from 3 to 6.

The M" units are preferably selected from alkenes of up to about 10 carbon atoms, such as decene. The amount of functionality provided in these phenol-modified silicones can be controlled by controlling the ratio of M' to M" units, i.e. the ratio of y to z.

In a preferred embodiment of the present invention, the ratio of M' units to silicon atoms is less than 2:1 and it is more preferred that this ratio be no greater than 1. When the silicone composition has the formula $Q_p(Si(CH_3)_2M')_y(Si(CH_3)_2M")_z$ the ratio of the sum of y+z to p does not exceed 4:1, preferably is from about 1:1 to 4:1 and more preferably is from about 1.5:1 to about 2.5:1.

These phenol-modified silicones are generally prepared by adding a vinyl-containing phenol to the silicone hydride precursor of the phenol silicone, which is synthesized according to methods known to those skilled in the art by reacting a polydialkylsiloxane, preferably a polydimethylsiloxane, containing alkyltrisiloxy functionalities, cyclic tetramer functionalities and tetrasiloxy functionalities, and other reactants such as M" precursors, in the presence of a catalyst under acidic conditions. They may also be prepared by the hydrolysis of corresponding phenol functional chlorosilanes.

The branched and cyclic phenol-modified silicones of the present invention remain liquid at temperatures as low as −80° and are lower in viscosity temperatures below −40° C. than linear phenol-modified silicones of the same molecular weight. In their stable liquid form the phenol-modified silicones of the present invention are ideal candidates for treating leather, fabric and paper where resistance to mildew and rot is desired.

DESCRIPTION OF THE PREFERRED EMBODIMENTS

The following examples illustrate the present invention. They are not to be construed to limit the scope of the claims in any manner whatsoever.

EXAMPLE 1

354 g of a trifunctional siloxane hydride fluid ($TD_{12}M_3^H$) was added to a 1 liter flask and heated while stirring to 50° C. A platinum catalyst (0.005 g) was then added followed by the slow addition of 150.6 g of eugenol. The reaction was allowed to run for two hours at which time, infra-red spectroscopy indicated that the silicone hydride had disappeared.

The product was passed through a thin film evaporator to yield a slightly yellow, slightly hazy fluid having a viscosity of 100 centistokes.

EXAMPLE 2

1817 g of branched hydride ($TD_{15}M_3^H$) were reacted with 668.5 g of eugenol and 0.02 g of a platinum catalyst as described in Example 1, except that the reaction temperature was raised to 80° C. The final product was slightly yellow and slightly hazy in appearance, having a viscosity of 93.4 centistokes.

EXAMPLE 3

The procedure of Example 2 was followed using 1964 g of $TD_{30}M_3^H$, 0.02 g of catalyst and 400 g of eugenol. The appearance of the final product was slightly hazy and slightly yellow. The product fluid had a viscosity of 82.1 centistokes.

EXAMPLE 4

The procedure of Example 2 was followed using 627 g of $TD_{50}M_3^H$, 0.01 g of catalyst and 80 g of eugenol. The reacted material was not thin film evaporated, and the product was slightly yellow and slightly hazy in appearance. The product fluid had a viscosity of 79 centistokes.

EXAMPLE 5

To a 3 liter pot is added 264 grams of a mixture of methyl hydride substituted cyclic siloxanes of the formula $(CH_3HSiO)_b$ wherein b is 3 (1.5 weight percent), 4 (45.0 weight percent), 5 (40 weight percent) and 6 (5.0 weight percent) inclusive. 500 grams of toluene is added and the mixture is azeotroped dry at toluene reflux. The mixture is then cooled to 100° C., and 0.3 grams of platinum catalyst (see, Lamoreaux, U.S. Pat. No. 3,220,972) are added.

To this mixture is added a solution of 500 grams of toluene and 736 grams of eugenol, which was previously dried and filtered. The temperature is maintained at 100°–115° C. during the exotherm. After all of the toluene/eugenol was added, the mixture was allowed to cook for 3 hours at 100° C. until infra red spectroscopy confirmed disappearance of all silicone hydride functionality. The toluene was stripped at 150° C. pot temperature under 10 mm vacuum. The final product has a slight haze and a gum-like consistency.

EXAMPLE 6

To a 500 ml beaker is added 26 grams of 98 percent pure tetra methylcyclo tetrasiloxane (methylhydrogen tetramer). 0.01 grams of platinum catalyst (Lamoreaux) is added to the tetramer. 74 grams of eugenol is then added dropwise and the exotherm rose to 150° C. The product has a gum like consistency as with Example 4.

EXAMPLE 7

250 g of $M^HQ$ resin is added to a flask containing 250 g of toluene. To this is added 0.33 g of platinum catalyst and 106 g of eugenol. The mixture is allowed to react for 1 hour. 284 g of 1-decene is then added and allowed to react for 1 hour. The solvent is removed leaving a product of the formula M'M"Q.

EXAMPLE 8

A $TD_{50}M'$ branched eugenol modified siloxane is prepared according to the procedures of Example 1. For comparative purposes a linear $MD_{50}M'$ eugenol modified siloxane is also prepared. The two specimens are tested for low temperature viscosity by placing the specimens in an acetone/dry ice bath.

At −80° C. it is observed that the linear siloxane turns solid, but the branched siloxane remains pourable at this temperature.

Viscosity measurement at −54° C. were then taken of the materials with the following results:
linear: 1917 centistokes
branched: 72 centistokes.

From the data above, it can be seen that the branched materials provide significantly improved low temperature viscosity properties over the linear materials.

EXAMPLE 9

Into a 50 cc 1 neck R.B. flask equipped with a magnetic stirrer bar and a reflux condenser was placed 3.30 g of eugenol along with 20 μl of Karstedt's catalyst (see U.S. Pat. No. 3,715,334) and 25 cc of $CH_2Cl_2$. To this was added 1.21 g of $D_4^H$ (molecular weight 240.5). The reaction mixture quickly exothermed to reflux. After 30 minutes, the reacted mixture was analyzed by $^1H$ NMR. There was a small amount of eugenol present but no remaining silane hydride.

The reaction mixture was stripped of $CH_2Cl_2$ and the product transferred to a 5 cc round bottom flask with a distillation head. The product was stripped at 150° C. at a pressure of 0.15 millimeters of mercury. $^1H$-NMR of the stripped product showed the eugenol to be gone. The yield of product was 3.36 g.

EXAMPLE 10

Methyl(tris-dimethylsiloxyethyl(2-(4-acetoxybenzene))silane(tris-acetate siloxane)is prepared by placing into a 4 dram vial equipped with a magnetic stirrer bar 4.96 g of p-acetoxystyrene, along with 20 μl of Karstedt's catalyst. To the stirred solution is then added 2.69 g of methyl(tris-dimethylsiloxy)silane. The reaction mixture was allowed to exotherm and after 1.5 hours $^1H$ NMR analysis showed no silane and only a small amount of olefin remained.

Into a 50 cc 1 neck round bottom flask equipped with a magnetic stirrer bar and $N_2$ bypass was placed 3.8 g of tris-acetate siloxane prepared as above, 25 cc methanol, 0.27 g of water and 2.08 g of $K_2CO_3$. After stirring for 0.5 hours, a small portion was sampled and $^1H$ NMR showed the hydrolysis to be complete. The reaction mixture was filtered and then methanol stripped. The residue was taken up in ether and washed once with dilute HCl and twice with water. After drying and removal of ether 2.45 g of methyl(tris-dimethylsiloxyethyl(2-(4-hydroxybenzene))silane was formed.

The above mentioned patents and publications are hereby incorporated by reference.

Many variations of the present invention will suggest themselves to those skilled in this art in light of the above detailed description. All such obvious modifications are within the full intended scope of the appended claims.

We claim:

1. A silicone composition comprising branched silicones of the general formula:

wherein T is a trifunctional alkyl siloxy unit of the general formula $RSiO_{3/2}$ where R is an alkyl group of from 1 to about 20 carbon atoms; D represents an alkyl siloxy unit of the general formula $R_2SiO_{2/2}$ where R is as defined above, x is 0 or greater and M' is a phenol unit of the general formula

wherein $R^a$ is an alkylene group of from 2 to 12 carbon atoms and Y is selected from hydrogen, hydrocarbyl, hydrocarbyloxy or halogen.

2. A silicone composition as defined in claim 1 wherein $R^a$ is propylene and y is methoxy.

3. A silicone composition as defined in claim 1 wherein said R is methyl.

4. A silicone composition as defined in claim 1 wherein said x ranges from about 0 to about 300.

5. A silicone composition as defined in claim 2 wherein said x ranges from about 0 to about 100.

* * * * *